United States Patent
Kim et al.

(10) Patent No.: US 11,026,620 B2
(45) Date of Patent: Jun. 8, 2021

(54) SYSTEM AND METHOD FOR ESTIMATING ACUTE CEREBRAL INFARCTION ONSET TIME

(71) Applicants: THE ASAN FOUNDATION, Seoul (KR); UNIVERSITY OF ULSAN FOUNDATION FOR INDUSTRY COOPERATION, Ulsan (KR)

(72) Inventors: Namkug Kim, Seoul (KR); Hyun Na Lee, Seoul (KR); Sung Won Ham, Goyang-si (KR); Dong Wha Kang, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 163 days.

(21) Appl. No.: 16/417,159

(22) Filed: May 20, 2019

(65) Prior Publication Data

US 2019/0269359 A1     Sep. 5, 2019

Related U.S. Application Data

(63) Continuation of application No. PCT/KR2017/013073, filed on Nov. 17, 2017.

(30) Foreign Application Priority Data

Nov. 21, 2016    (KR) .................. 10-2016-0154688

(51) Int. Cl.
G06K 9/00    (2006.01)
A61B 5/00    (2006.01)
(Continued)

(52) U.S. Cl.
CPC .............. *A61B 5/4064* (2013.01); *A61B 5/00* (2013.01); *A61B 5/0042* (2013.01); *G06K 9/00* (2013.01);
(Continued)

(58) Field of Classification Search
None
See application file for complete search history.

(56) References Cited

U.S. PATENT DOCUMENTS 6,658,287 B1 * 12/2003 Litt ................. A61B 5/374
600/544
7,020,578 B2 * 3/2006 Sorensen ............ G06T 7/0012
424/9.36
(Continued)

FOREIGN PATENT DOCUMENTS

KR    10-2015-0030974 A    3/2015

OTHER PUBLICATIONS

Petkova et al., "MR imaging helps predict time from symptom onset in patients with acute stroke: implications for patients with unknown onset time." Radiology 257, No. 3 (2010): 782-792. (Year: 2010).*
(Continued)

*Primary Examiner* — Feng Niu
(74) *Attorney, Agent, or Firm* — Studebaker & Brackett PC

(57) ABSTRACT

The present disclosure relates to a system and a method for estimating an acute cerebral infarction onset time. The method according to the present disclosure includes at least: receiving a first image and a second image of a first patient whose acute cerebral infarction onset time is not identified; extracting an infarction area image from the second image; aligning the second image with the first image; defining an infarction area in the first image, based on a result of the alignment of the second image with the first image; extract-
(Continued)

ing feature information of the first patient, from the infarction area in the first image; comparing the extracted feature information with reference data; and calculating an amount of time that has elapsed since the acute cerebral infarction onset time, based on a result of the comparison of the extracted feature information with reference data.

12 Claims, 10 Drawing Sheets

(51) Int. Cl.
*G06T 7/11* (2017.01)
*G06T 7/00* (2017.01)
*G06T 7/33* (2017.01)
*A61B 5/055* (2006.01)

(52) U.S. Cl.
CPC .............. *G06T 7/00* (2013.01); *G06T 7/0008* (2013.01); *G06T 7/0014* (2013.01); *G06T 7/11* (2017.01); *A61B 5/055* (2013.01); *G06T 7/33* (2017.01); *G06T 2207/30016* (2013.01)

(56) References Cited

U.S. PATENT DOCUMENTS

| | | | | |
|---|---|---|---|---|
| 7,076,473 B2 * | 7/2006 | Moghaddam | ........ | G06K 9/6256 706/16 |
| 7,529,737 B2 * | 5/2009 | Aphinyanaphongs | .. | G06F 16/35 |
| 7,548,642 B2 * | 6/2009 | Odry | ..................... | G06T 7/0012 382/128 |
| 8,019,142 B2 * | 9/2011 | Nowinski | ............... | G06T 19/00 382/131 |
| 8,311,359 B2 * | 11/2012 | Volkau | ................... | G06T 7/344 382/262 |
| 8,787,638 B2 * | 7/2014 | Zee | ......................... | A61B 3/12 382/128 |
| 9,092,691 B1 * | 7/2015 | Beaumont | ............. | G06T 7/0014 |
| 9,639,933 B2 * | 5/2017 | Liang | ...................... | G06T 7/40 |
| 9,955,905 B2 * | 5/2018 | Intrator | ................... | A61B 5/726 |
| 10,463,271 B2 * | 11/2019 | Intrator | ................... | A61B 5/726 |
| 10,593,035 B2 * | 3/2020 | Onal | ....................... | G06T 7/0012 |
| 10,641,762 B2 * | 5/2020 | Dezawa | ............... | G01N 33/5073 |
| 10,846,620 B2 * | 11/2020 | Beers | .................... | G06K 9/6227 |
| 2006/0201504 A1 * | 9/2006 | Singhal | ................... | A62B 9/003 128/204.18 |
| 2009/0285466 A1 * | 11/2009 | Hipp | ....................... | G06T 7/0014 382/131 |
| 2010/0014755 A1 * | 1/2010 | Wilson | ................ | G06K 9/00604 382/173 |
| 2010/0221180 A1 * | 9/2010 | Wang | ....................... | A61K 51/04 424/1.77 |
| 2010/0290689 A1 * | 11/2010 | Gupta | .................... | G06T 7/0012 382/131 |
| 2014/0146155 A1 * | 5/2014 | Gibby | ..................... | G06T 7/0016 348/77 |
| 2015/0278470 A1 * | 10/2015 | Bakker | ................... | G16H 50/30 705/2 |
| 2016/0335432 A1 * | 11/2016 | Vatamanu | ............... | H04L 63/14 |
| 2017/0140551 A1 * | 5/2017 | Bauer | .................... | G06K 9/6256 |

OTHER PUBLICATIONS

Kim et al., KR 20150030974 A, published on Mar. 23, 2015 (machine translation) (Year: 2015).*
Kim et al., "Diffusion-weighted image and fluid-attenuated inversion recovery image mismatch: unclear-onset versus clear-onset stroke." Stroke 45, No. 2 (2014): 450-455. (Year: 2014).*
Gupta et al., "Automatic and rapid identification of infarct slices and hemisphere in DWI scans." Academic Radiology 15, No. 1 (2008): 24-39. (Year: 2008).*
Park, Byung-Rae et al "Implementation of Classification the Step in the Cerebral Infarction Using Neural Network in Magnetic Resonance Image". The Korean Society of Medical Informatics, Nov. 20, 2014 (http://kosmi.snubi.org/2004_fall/main.html ) See chapters II-III.
International Search Report issued in PCT/KR2017/013073; dated Mar. 23, 2018.

* cited by examiner

SYSTEM AND METHOD FOR ESTIMATING ACUTE CEREBRAL INFARCTION ONSET TIME

CROSS-REFERENCE TO RELATED APPLICATIONS

The present application is a continuation of International Patent Application No. PCT/KR2017/013,073, filed Nov. 17, 2017 which is based upon and claims the benefit of priority to Korean Patent Application No. 10-2016-0154688 filed on Nov. 21, 2016. The disclosures of the above-listed applications are hereby incorporated by reference herein in their entirety.

RELATED ART

Embodiments of the inventive concept relate to an acute cerebral infarction onset time estimation system and method. More specifically, embodiments of the inventive concept relate to a system and a method, for estimating an amount of time that has elapsed time since an onset time of acute cerebral infarction of a patient whose acute cerebral infarction onset time has not been identified, by using a magnetic resonance imaging (MRI) technology.

Thrombolysis, which prevents damages to brain cells by helping blood-communication in occluded cerebral blood vessels due to thrombus or embolus, is widely known as a method for treating patients with acute cerebral infarction. Thrombolysis should be performed as soon as possible from the start point of cerebral infarction, since the thrombolysis must be done promptly before the brain cells are damaged.

However, the majority of patients who come to hospitals have no information about an onset time of acute cerebral infarction thereof. In other words, after a patient falls down, the patient is found by another person and transferred to a hospital. Thus, it may not be accurately checked when the acute cerebral infarction started before the patient was discovered by another person. In this case, there is a shortage of specialists who can judge whether the patient would be able to be subjected to thrombolysis only based on reading medical images (i.e., MR images).

In addition, in emergency rooms where patients with acute cerebral infarction were transferred, the number of medical staffs experienced in the acute cerebral infarction is small.

Therefore, there is a need for an invention that provides information that allows clinicians to safely and quickly determine the feasibility of treatment for patients with acute cerebral infarction.

SUMMARY

Embodiments of the inventive concept are to provide an acute cerebral infarction onset time estimation system and method, by which an infarction region is automatically analyzed using characteristics of a diffusion-weighted image and a fluid-attenuated inversion recovery image of Magnetic Resonance Image (MRI) of the acute cerebral infarction patient, then, an amount of time that has elapsed since starting the acute cerebral infarction is estimated based on feature information in the infarction region, and, then, the estimated amount of time is provided to the clinician to quickly determine whether the acute cerebral infarction of the patient can be treated.

Purposes presented by the embodiments of the inventive concept are not limited to the purpose set forth above, and other purposes not mentioned may be clearly understood by one of ordinary skill in the art from the following description.

According to exemplary embodiments of the present disclosure, a method for estimating an onset time of acute cerebral infarction includes at least: receiving from and external device, a first image and a second image of a first patient whose acute cerebral infarction onset time is not identified, the first image is a fluid-attenuated inversion recovery image, and the second image is a diffusion-weighted image; extracting an infarction region image from the second image; aligning the second image with the first image; defining an infarction region in the first image, based on a result of the alignment of the second image with the first image; extracting feature information of the first patient, from the infarction region in the first image; comparing the extracted feature information with reference data; and calculating an amount of time that has elapsed since the acute cerebral infarction onset time, based on a result of the comparison of the extracted feature information with the reference data.

According to other exemplary embodiments of the present disclosure, a system for estimation of an acute cerebral infarction onset time includes at least: an image storage that stores a first image and a second image of a first patient whose acute cerebral infarction onset time is not identified, wherein the first image is a fluid-attenuated inversion recovery image, and the second image is a diffusion-weighted image; an infarction region image extractor that extracts an infarction region image from the second image; an image aligner that aligns the second image with the first image; an infarction region definer that defines an infarction region in the first image, based on a result of the alignment of the second image with the first image; a feature information extractor that extracts feature information of the first patient, from the infarction region of the first image; and an elapsed amount of time calculator that compares the extracted feature information with reference data, and calculates an amount of time that has elapsed since the acute cerebral infarction onset time, based on a result of the comparison of the extracted feature information with reference data.

According to the inventive concept as described above, the acute cerebral infarction onset time can be estimated from a patient whose acute cerebral infarction onset time has not been identified. This may reduce the number of patients who miss the timing of thrombolysis due to the inability to determine whether the acute cerebral infarction is capable of be cured using thrombolysis.

Further, the above described embodiments related to the method can be performed by a computer including a processor. Since a computer quickly performs the elapsed time amount calculation of the acute cerebral infarction automatically based on the fluid-attenuated inversion recovery (FAIR) image and the diffusion-weighted image, the medical staff may figure out the elapsed duration after the patient's acute cerebral infarction starts, and may determine immediately whether to start the thrombolysis for the patient. Therefore, a time required for the medical staff to determine whether or not the thrombolysis is performed using the MR image reading may be reduced. This can increase the percentage of patients whose acute cerebral infarction can be treated.

BRIEF DESCRIPTION OF DRAWINGS

The above and other objects and features will become apparent from the following description with reference to the following figures, wherein like reference numerals refer to like parts throughout the various figures unless otherwise specified, and wherein.

DETAILED DESCRIPTION

Figure 1:
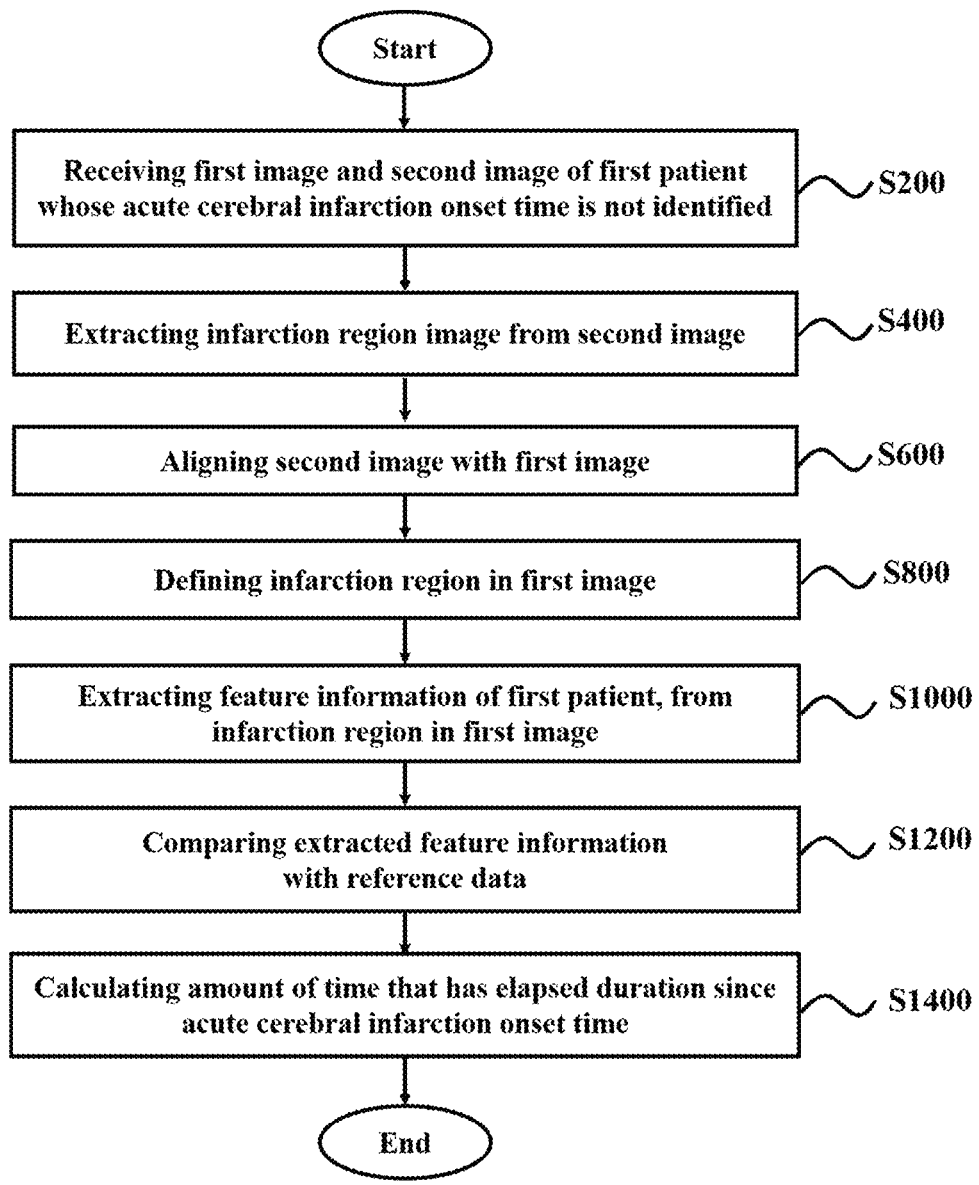
FIG. 1 is a flowchart of an acute cerebral infarction onset time estimation method, according to some embodiments of the present disclosure.

According to exemplary embodiments, a method for estimating an onset time of acute cerebral infarction includes: receiving a first image and a second image of a first patient whose acute cerebral infarction onset time is not identified, the first image is a fluid-attenuated inversion recovery image, and the second image is a diffusion-weighted image; extracting an infarction region image from the second image; aligning the second image with the first image; defining an infarction region in the first image, based on a result of the alignment of the second image with the first image; extracting feature information of the first patient, from the infarction region in the first image; comparing the extracted feature information with reference data; and calculating an amount of time that has elapsed since the acute cerebral infarction onset time, based on a result of the comparison of the extracted feature information with the reference data.

Further, according to some exemplary embodiments, the reference data includes feature information of at least one second patient, contained in an infarction region of a first image of the at least one second patient. The second patient is a patient whose acute cerebral infarction onset time is identified. The reference data further includes information on an amount of time that has elapsed since an acute cerebral infarction onset time of the at least one second patient.

Further, according to some exemplary embodiments, the extracting of the infarction region image from the second image comprises: normalizing an intensity of an apparent diffusion coefficient map of the second image; and extracting the infarction region image via an absolute reference value search in the normalized apparent diffusion coefficient map.

Further, according to some exemplary embodiments, the method further comprises: comparing the infarction region with a symmetric region located in a brain of the first patient and being symmetrical to the infarction region; and extracting a relative signal amount of the infarction region, based on a result of the comparison of the infarction region with the symmetric region.

Further, according to some exemplary embodiments, the method further comprises generating a ratio map that includes a visual expression of a relative signal amount between the symmetric region and the infarction region.

Further, according to some exemplary embodiments, the feature information includes: first feature information extracted from the infarction region in the first image; and second feature information extracted from an infarction region in the ratio map for the first image.

Further, according to some exemplary embodiments, the method further comprises: determining whether the elapsed amount of time is within a reference duration; and outputting a signal for notifying the determination result.

Further, according to some exemplary embodiments, the aligning of the second image with the first image comprises aligning of the second image with the first image by applying at least one of an enlargement, a shrinkage, a symmetrical movement, and a rotation, to the first image or the second image, based on a skeleton position in the first image or the second image.

Further, according to some exemplary embodiments, the extracting of the feature information comprises extracting the feature information by applying at least one of a gray level co-occurrence matrix, a run-length matrix and a local binary pattern to signal intensity and gradient of the infarction region.

Further, according to some exemplary embodiments, the method further comprises generating the reference data as a support vector machine, based on first and second images of a plurality of second patients. The generating of the reference data comprises: classifying the plurality of second patients into a training group, a validating group, and a testing group; extracting feature information of each of second patients classified into the training group, from a first image of the each of the second patients classified into the training group, by performing an alignment of the first image of the each of the second patients classified into the training group with a second image of the each of the second patients classified into the training group; training the support vector machine by using the feature information of the second patients classified into the training group; determining a type of the support vector machine by using the validating group; and applying the testing group to the determined support vector machine type to determine whether the determined support vector machine type is to be defined as the reference data.

Further, according to some exemplary embodiments, the reference data is classified into detailed groups according to gender or age information of the second patients. In some exemplary embodiments, the calculating of the elapsed amount of time comprises defining detailed groups to be compared with the feature information of the first patient based on age information or gender information of the first patient.

According to some exemplary embodiments, a system for estimation of an acute cerebral infarction onset time comprises: an image storage that stores a first image and a second image of a first patient whose acute cerebral infarction onset time is not identified, the first image is a fluid-attenuated inversion recovery image, and the second image is a diffusion-weighted image; an infarction region image extractor that extracts an infarction region image from the second image; an image aligner that aligns the second image with the first image; an infarction region definer that defines an infarction region in the first image, based on a result of the alignment of the second image with the first image; a feature information extractor that extracts feature information of the first patient, from the infarction region of the first image; and an elapsed amount of time calculator that compares the extracted feature information with reference data, and calculates an amount of time that has elapsed since the acute cerebral infarction onset time, based on a result of the comparison of the extracted feature information with reference data.

Further, according to some exemplary embodiments, the reference data includes feature information of at least one second patient, contained in an infarction region of a first image of the at least one second patient, the second patient is a patient whose acute cerebral infarction onset time is identified; and information on an amount of time that has elapsed since an acute cerebral infarction onset time of the at least one second patient.

Further, according to some exemplary embodiments, the system further comprises: a reference data generator that generates the reference data as a support vector machine, based on first and second images of a plurality of second patients. In some exemplary embodiments, the reference data generation module is configured to: classify the plurality of second patients into a training group, a validating group, and a testing group; extract feature information of each of second patients classified into the training group from a first image of the each of the second patients classified into the training group, by performing an alignment of the first image of the each of the second patients classified into the training group with a second image of the each of the second patients classified into the training group; train the support vector machine by using the feature information of the second patients classified into the training group; determine a type of the support vector machine by using the validating group; and apply the testing group to the determined support vector machine type to determine whether the determined support vector machine type is to be defined as the reference data.

Further, according to some exemplary embodiments, the system further includes a ratio map generator configured to: compare the infarction region with a symmetric region located in a brain of the first patient and being symmetrical to the infarction region; extract a relative signal amount of the infarction region, based on a result of the comparison of the infarction region with the symmetric region; and generate a ratio map that includes a visual expression of a relative signal amount between the symmetric region and the infarction region. The feature information includes: first feature information extracted from the infarction region in the first image; and second feature information extracted from an infarction region in the ratio map for the first image.

According to some exemplary embodiments, a non-transitory computer readable recording medium storing a computer program coupled to a computer device including a processor to execute the method for estimating an onset time of acute cerebral infarction, as described above.

Hereinafter, some embodiments of the present disclosure will be described in detail with reference to the accompanying drawings. Advantages and features of the inventive concept, and methods of accomplishing the same, will become apparent with reference to the embodiments described in detail below with reference to the accompanying drawings. However, the inventive concept is not limited to the embodiments disclosed below, but may be embodied in various forms. These embodiments are provided so that the present disclosure is fully explained, and that it is believed that the disclosure is intended to be sufficiently understood by one of ordinary skill in the art which the present disclosure belongs. The inventive concept is only defined by the scope of the claim. Like reference numerals refer to like elements throughout the specification.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof.

As used herein, "first image 10" is referring to a fluid-attenuated inversion recovery image (FLAIR image).

As used herein, "second image 20" is referring to a diffusion-weighted image (DWI image).

As used herein, "first patient" is referring to a patient whose acute cerebral infarction onset time is not identified. In other words, the "first patient" is referring to a patient whose acute cerebral infarction onset time should be identified by the computer. By contrast, "second patient" is referring to a patient whose acute cerebral infarction onset time is identified.

As used herein, "computer" or "processor" is referring to all of the various devices that can perform computational processing and visually present the processing results to the user. For example, the "computer" or "processor" includes not only a desktop PC, a note book, but also a smart phone, a tablet PC, a cellular phone, a personal communication service phone (PCS phone), a mobile terminal that performs a IEEE 802.11 communication, such as Wi-Fi, and cellular communication, such as 3G, 4G, 5G, LTE, LTE-A, or WiMAX, a Palm personal computer, a personal digital assistant (PDA), etc. Further, the "computer" or "processor" also includes medical equipment that acquires or views an angiographic image.

Hereinafter, each of an acute cerebral infarction onset time estimation system and a method, according to embodiments of the present disclosure will be described in detail with reference to the drawings.

FIG. 1 is a flowchart of the acute cerebral infarction onset time estimation method according to some embodiments of the present disclosure.

Figure 2:
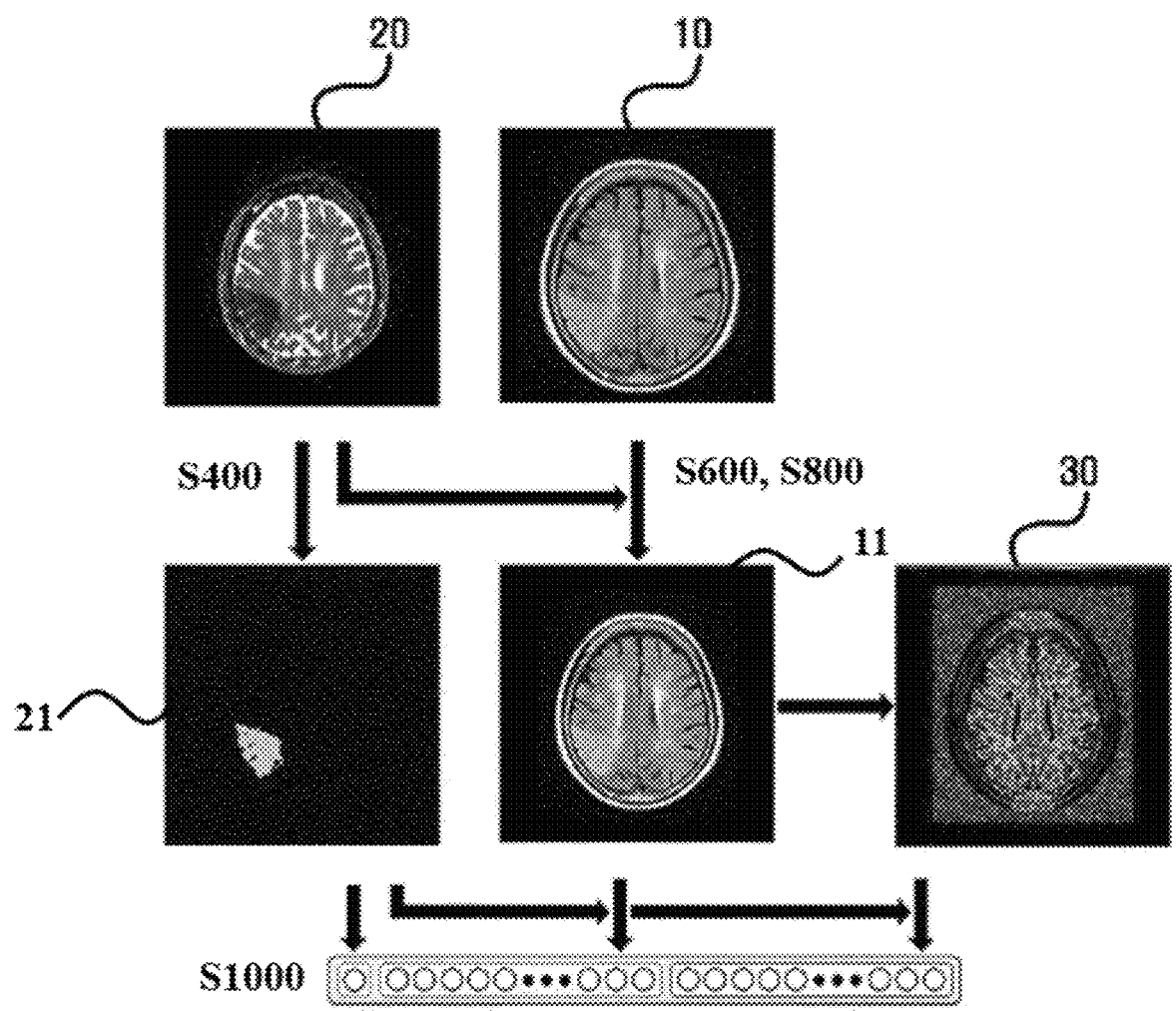
FIG. 2 shows an example of a process for applying the acute cerebral infarction onset time estimation method to a first image and a second image, according to some embodiments of the present disclosure.

FIG. 2 shows an example of a process of applying the acute cerebral infarction onset time estimation method to a first image and a second image according to some embodiments of the present disclosure.

Referring to FIG. 1, the acute cerebral infarction onset time estimation method according to some embodiments of the present disclosure comprises a step S200 of receiving a first image 10 and a second image 20 of a first patient whose acute cerebral infarction onset time is not identified; a step S400 of extracting an infarction region image from the second image 20; a step S600 of aligning the second image with the first image 10; a step S800 of defining an infarction region in the first image, based on a result of the alignment of the second image with the first image; a step S1000 of extracting feature information of the first patient, from the infarction region in the first image 10; a step S1200 of comparing the extracted feature information with reference data; and a step S1400 of calculating an amount of time that has elapsed since the acute cerebral infarction onset time. In some embodiments, each of the above described steps is performed by a computer or a processor. According to the above described operations, as shown in FIG. 2, based on the first image 10, which is a fluid-attenuated inversion recovery image, and the second image 20, which is a diffusion-weighted image, an infarction region image 21 is extracted, and an infarction region is defined in a registered fluid-attenuated inversion recovery image 11. Further, a ratio map 30 is generated based on the registered fluid-attenuated inversion recovery image 11, and feature information 40 is extracted.

Hereinafter, a detailed description of each operation will be described.

In some embodiments, the diffusion-weighted image (i.e., DWI image), which is the second image 20, shows an acute cerebral infarction area within a short time after the acute cerebral infarction occurs and thus a person who views the diffusion-weighted image would be able to immediately identify an acute cerebral infarction range. On the other hand, in the fluid-attenuated inversion recovery image (i.e., FLAIR image), which is the first image 10, the acute cerebral infarction area is gradually darkened over time after the acute cerebral infarction onset time. In other words, in the fluid-attenuated inversion recovery image, which is the first image 10, an expression level of the infarction region in the acute cerebral infarction varies based on an elapsed duration since the acute cerebral infarction onset time. Therefore, the present disclosure identifies an amount of time that has elapsed since the acute cerebral infarction onset time based on the discrepancy between the DWI image and the FLAIR image.

In some embodiments, in the step S200 (image receiving operation), the processor including a processor receives the first image 10 and the second image 20 for a first patient whose acute cerebral infarction onset time is not identified. In some embodiments, the processor directly receives medical image data taken from a magnetic resonance imaging (MRI) device.

Alternatively, in some other embodiments, the processor downloads medical image data from another computer or an external server and store the received image data in the computer. For example, when the medical staff determines the amount of the time that has elapsed since the acute cerebral infarction of a patient entering the emergency room due to the acute cerebral infarction and intends to make an emergency treatment plan, the processor receives a MR image of the patient directly from the magnetic resonance imaging (MRI) device.

Figure 3:
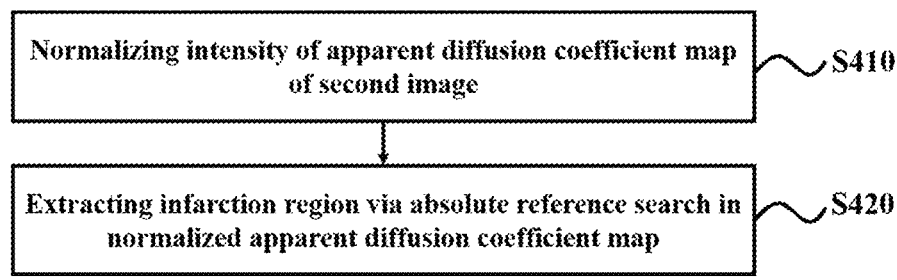
FIG. 3 is a flowchart of an infarction region image extraction process, according to some embodiments of the present disclosure.

In some embodiments, in the step S400, the processor extracts the infarction region image from the second image 20. In other words, in some embodiments, the processor identifies a boundary of the infarction region within the second image 20 (i.e., DWI image) and extracts the infarction region image based on the identified boundary. In some embodiments, as in FIG. 3, the step S400 of infarction region image extracting operation comprises a step S410 of normalizing an intensity of an apparent diffusion coefficient map of the second image 20; and a step S420 of extracting an infarction region via an absolute reference search in the normalized apparent diffusion coefficient map. Because the infarction region looks as a dark region in the apparent diffusion coefficient (ADC) map, the processor determines a dark pixel below or equal to a certain threshold value as the infarction region. The processor performs a process of normalizing the intensity of the signal within the ADC image map, since there occur differences between brightness distributions of the ADC image maps between individuals. Thereafter, the processor sets, as an absolute value, a threshold to act as a reference value for the infarction region in a normalized ADC image map.

In some embodiments, in the step S600, the processor aligns the second image 20 with the first image 10, and in the step S800, the processor defines the infarction region in the first image 10, based on a result of the alignment of the second image 20 with the first image 10.

First, in the step S600, the processor aligns the second image 20 to the first image 10. In some embodiments, the processor performs the alignment based on a position of a skeleton in the first image 10 and the second image 20. A brain skeleton structure of the same patient is the same even when there is a difference between manners in which MR images are taken. Thus, the processor performs the alignment based on the skeleton location or structure in the first image 10 and second image 20. The processor performs the alignment by applying at least one of an enlargement, a shrinkage, a symmetrical movement, and a rotation, to the first image 10 or second image 20. Because there is a difference between brain shapes in the first image 10 and second image 20 when there is a change in a patient posture at the time of capturing the first image 10 and second image 20, the processor performs the alignment by applying at least one of an enlargement, a shrinkage, a symmetrical movement, and a rotation, to the first image 10 or second image 20.

Next, in the step S800, the processor then defines the infarction region in the first image 10, based on a result of the alignment of the second image with the first image (based on the infarction region in the second image 20). A boundary of the infarction region within the diffusion-weighted image (i.e., DWI image) in which the infarction region of the acute cerebral infarction patient appears within a short period of time since the onset time is superimposed on the fluid-attenuated inversion recovery image (i.e., FLAIR image), thereby to define an infarction region in the FLAIR image.

In some embodiments, in the step S1000, the processor extracts feature information of the first patient, from the infarction region of the first image 10. The feature information includes at least one feature element extracted from within a specific region of the image data (i.e., MR image). In some embodiments, the step S1000 of extracting the feature information is performed by applying at least one of Gray Level Cooccurrence Matrix (GLCM), Run-Length Matrix (especially, Gray Level Run-Length Matrix (GLRLM)), and Local Binary Pattern (LBP), to the signal intensity and gradient of the infarction region.

Specifically, the feature information includes various information that is acquired from the infarction region in the second image 20. In some embodiments, the feature information includes size or volume information of the infarction region. Further, in some embodiments, the feature information includes a mean, a standard deviation, a skewness, and kurtosis calculated for a signal intensity, a signal gradient, and a local binary pattern (LBP) map in the infarction region. Further, in some embodiments, the feature information includes various feature elements obtained by applying a Gray Level Cooccurrence Matrix or Run-Length Matrix. For example, when the processor applies the Gray Level Cooccurrence Matrix or Run-Length Matrix, all or some of the feature elements as shown in [Table 1] are acquired and used as feature information.

TABLE 1

| Extraction scheme | Available feature elements |
| --- | --- |
| GLCM | energy, entropy, dissimilarity, contrast, inverse difference, correlation, homogeneity, autocorrelation, cluster shade, cluster prominence, maximum probability, sum of squares, sum average, sum variance, sum entropy, difference variance, difference entropy, information of correlation1 (IOC1), information of correlation2 (IOC2), inverse difference normalized (INN), inverse difference moment normalized (IDN) |
| GLRLM | short run emphasis (SRE), long run emphasis (LRE), gray-level nonuniformity (GLN), run-length nonuniformity (RLN), run percentage (RP), low gray run emphasis (LGRE), high gray run emphasis (HGRE), short run low gray emphasis (SRLGE), short run high gray emphasis (SRHGE), long run low gray emphasis (LRLGE), long run high gray emphasis (LRHGE) |

In some embodiments, in the step S1200, the processor thereafter compares the extracted feature information with the reference data, and in the step S1400, the processor calculates the amount of time that has elapsed since the acute cerebral infarction onset time. That is, in some embodiments, the processor calculates the elapsed amount of time after the acute cerebral infarction onset of the first patient, based on the feature information in the infarction region, identified by the second image 20 (i.e., DWI image), in the first image 10 (i.e., FLAIR image). For example, the feature information in the infarction region contains information about a degree to which the infarction region is darkened in the FLAIR image, or information about an image shape that appears in the infarction region. The reference data includes feature information of at least one second patients whose acute cerebral infarction onset time is identified, contained in the infarction region of the first image 10 and information on an amount of time that has elapsed since an acute cerebral infarction onset time of the at least one second patient. In some embodiments, the processor searches the reference data for the feature information of the second patients corresponding to the feature information of the first patient. In some embodiments, the processor determines the elapsed amount of time after onset of the second patients' acute cerebral infarction as the elapsed amount of time after onset of the acute cerebral infarction for the first patient. In some embodiments, the processor generates the reference data as a Support Vector Machine (SVM) as described below. The processor applies, to the SVM, the elapsed duration since onset of the acute cerebral infarction of the first patient whose acute cerebral infarction onset time should be identified, thereby to calculate the elapsed duration since the onset of the acute cerebral infarction of the first patient.

Further, in some embodiments of the present disclosure, the method further comprises a step S1300 (not shown in the drawings), of determining whether or not the elapsed duration is within a reference duration, and a step S1500 (not shown in the drawings) of outputting a signal for notifying the determination result. In some embodiments, the acute cerebral infarction treatment performance plan varies depending on whether or not the elapsed duration is within the reference duration. Therefore, when the processor informs the medical staff quickly whether a certain time (e.g., 4.5 hours or 6 hours) has elapsed after the acute cerebral infarction has been started, the medical staff promptly establishes the treatment plan. The acute cerebral infarction patients have different treatment options depending on the elapsed durations from the onset times of the acute cerebral infarction of the patients. An intravenous recombinant tissue plasminogen activator (rt-PA)-based treatment is available for a patient whose elapsed duration since the onset of the acute cerebral infarction is up to 4.5 hours. An intra-arterial mechanical thrombectomy is effective for a patient whose elapsed duration since the onset of the acute cerebral infarction is up to 6 hours. Therefore, in order for the medical staff to quickly determine the treatment scheme and proceed with the determined treatment scheme, the processor according to some embodiments of the present disclosure informs the medical staff quickly of whether or not the elapsed amount of time since the onset of the acute cerebral infarction of the first patient is within the reference duration.

Figure 4:
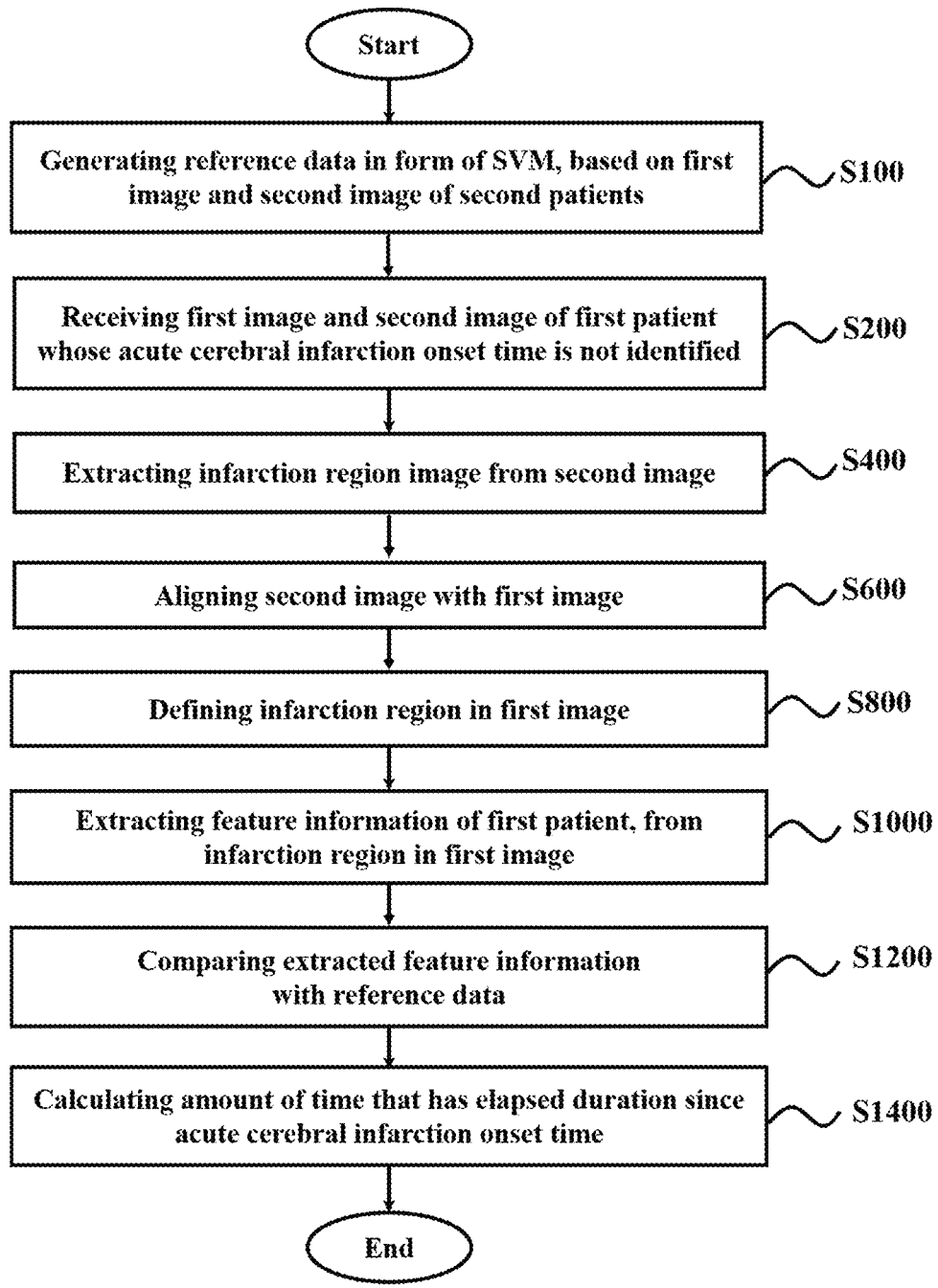
FIG. 4 is a flowchart of the acute cerebral infarction onset time estimation method that further includes a reference data generation operation, according to some embodiments of the present disclosure.

Further, in some embodiments of the present disclosure, as shown in FIG. 4, the method comprises a step S100 of generating the reference data in a form of a support vector machine (SVM), based on first and second images 10 and 20 of a plurality of second patients. That is, in some embodiments, the processor generates a SVM for performing machine learning based on feature information about a plurality of second patients as constructed as big data. In some embodiments, the feature information for the second patients is obtained in the same manner as in acquiring the feature information for the first patient. That is, the processor aligns the first image 10 and the second image 20 for each second patient with another second patient, defines an infarction region by applying an infarction region identified in the second image 20 to the first image 10, and extracts feature information from the defined infarction region.

Figure 5:
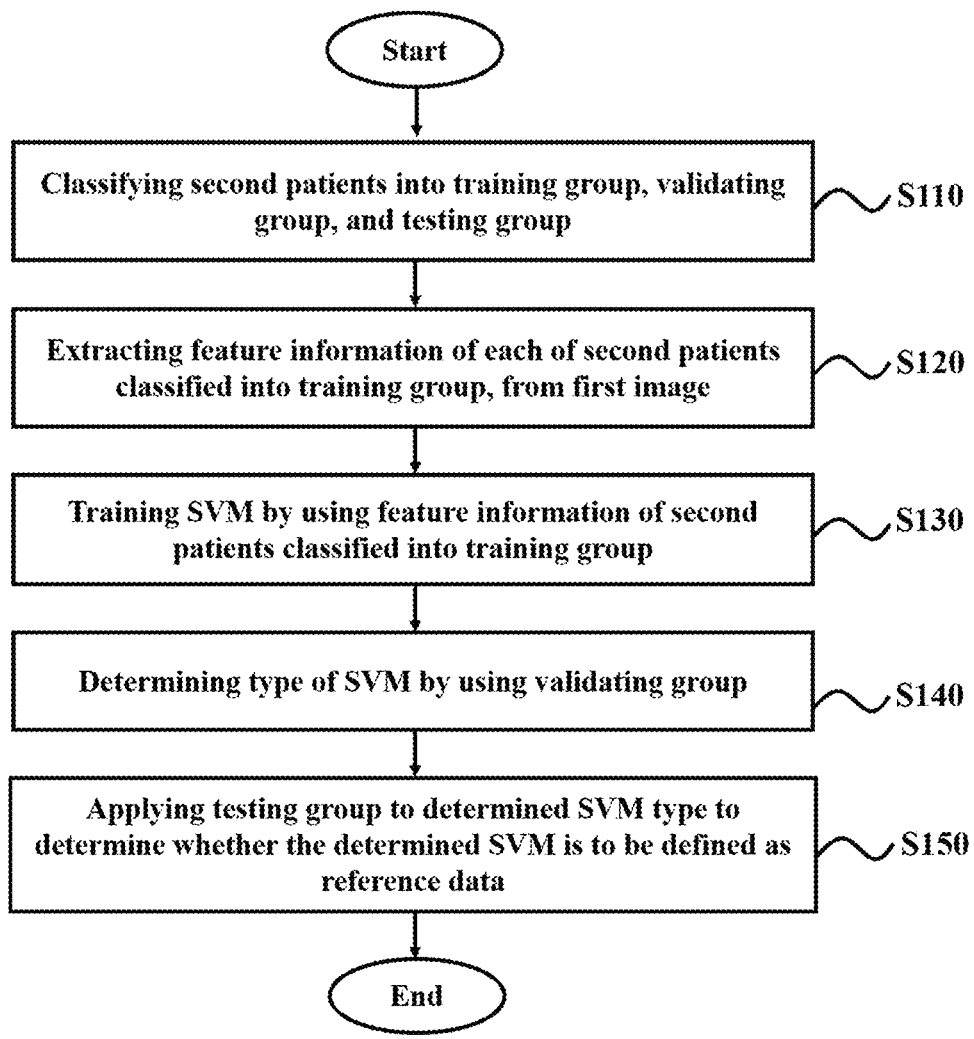
FIG. 5 is a flowchart showing a process of generating reference data in a form of Support Vector Machine (SVM), according to some embodiments of the present disclosure.

In some embodiments, the step S100 (the reference data generation operation) comprises, as shown in FIG. 5, a step S110 of classifying the plurality of second patients into a training group, a validating group, and a testing group; a step S120 of extracting feature information of each of second patients classified into the training group, from a first image 10 of the each of the second patients classified into the training group, by performing an alignment of the first image of the each of the second patients classified into the training group with a second image of the each of the second patients classified into the training group; a step S130 of training the support vector machine by using the feature information of the second patients classified into the training group; a step S140 of determining a type of the support vector machine by using the validating group; and a step S150 of applying the testing group to the determined support vector machine type to determine whether the determined support vector machine type is to be defined as the reference data. That is, when the feature information of the second patient to be subjected to training to generate the SVM is used for the SVM selection and verification, it is possible that the SVM appropriateness examination is not performed properly. Thus, the processor classifies a plurality of second patients into the training group (e.g., 60% of the entire second patients), the validating group (for example, 20% of the entire second patients), and the testing group (for example, 20% of the entire second patients). Then, a particular type of SVM is selected by applying the information of the second patients classified into the validating group to SVMs computed via training using the training group. Then, feature information of the second patients classified into the testing group is applied to the selected type of SVM to evaluate whether the selected type of SVM corresponds to an optimal SVM. Thus, it is determined whether the selected type of SVM is to be defined as the reference data.

Further, in some embodiments of the present disclosure, the reference data is classified into detailed groups based on the gender or age information of the second patients. There occur differences between state changes over time after onset time of acute cerebral infarction based on gender or age of patient. Therefore, in order to accurately calculate the elapsed amount of time, based on the age and gender of the first patient, the processor classifies a plurality of second patients into a plurality of detailed groups based on the gender or age, and generates data for elapsed amount of time calculation for each detailed group. For example, the processor generates a SVM for each detailed group of the second patients. In this connection, the step S1200 (the elapsed amount of time calculation operation) comprises defining detailed groups to be compared with the feature information of the first patient, based on age information or gender information of the first patient.

Figure 6:
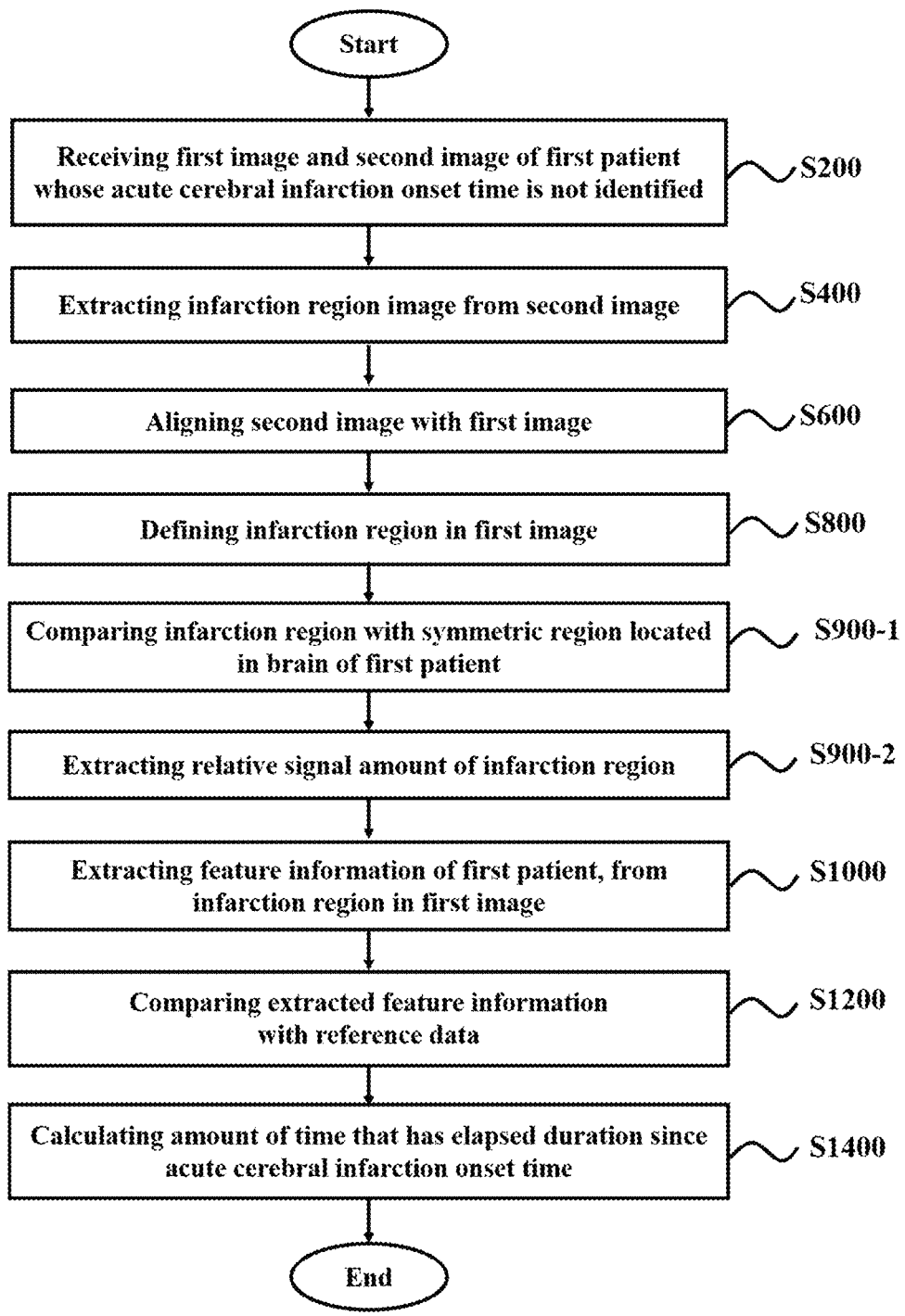
FIG. 6 is a flow chart of the acute cerebral infarction onset time estimation method which further includes a relative signal amount extracting operation of the first image according to some embodiments of the present disclosure.

Further, as shown in FIG. 6, in some embodiments of the present disclosure, the method further includes a step S900-1 of comparing the infarction region with a symmetric region located in a brain of the first patient and being symmetrical to the infarction region, and a step S900-2 of extracting a relative signal amount of the infarction region, based on a result of the comparison of the infarction region with the symmetric region. Since the MR image is represented using a relative signal amount within an image to be captured, it is possible that the signal amount of the infarction region is not an absolute signal amount. Therefore, using characteristics of the brain that the brain is symmetrically configured based on a specific boundary line, the processor compares the infarction region with a symmetric region located in a brain of the first patient and being symmetrical to the infarction region in the first image 10 to extract a relative signal amount of the infarction region. Therefore, as the relative signal amount of the infarction region in the first image 10 is calculated, the feature information extracted from the infarction region in the first image 10 of the first patient is compared with the feature information extracted from the infarction region of the first image 10 of the second patient, to improve accuracy of the present disclosure.

Figure 7:
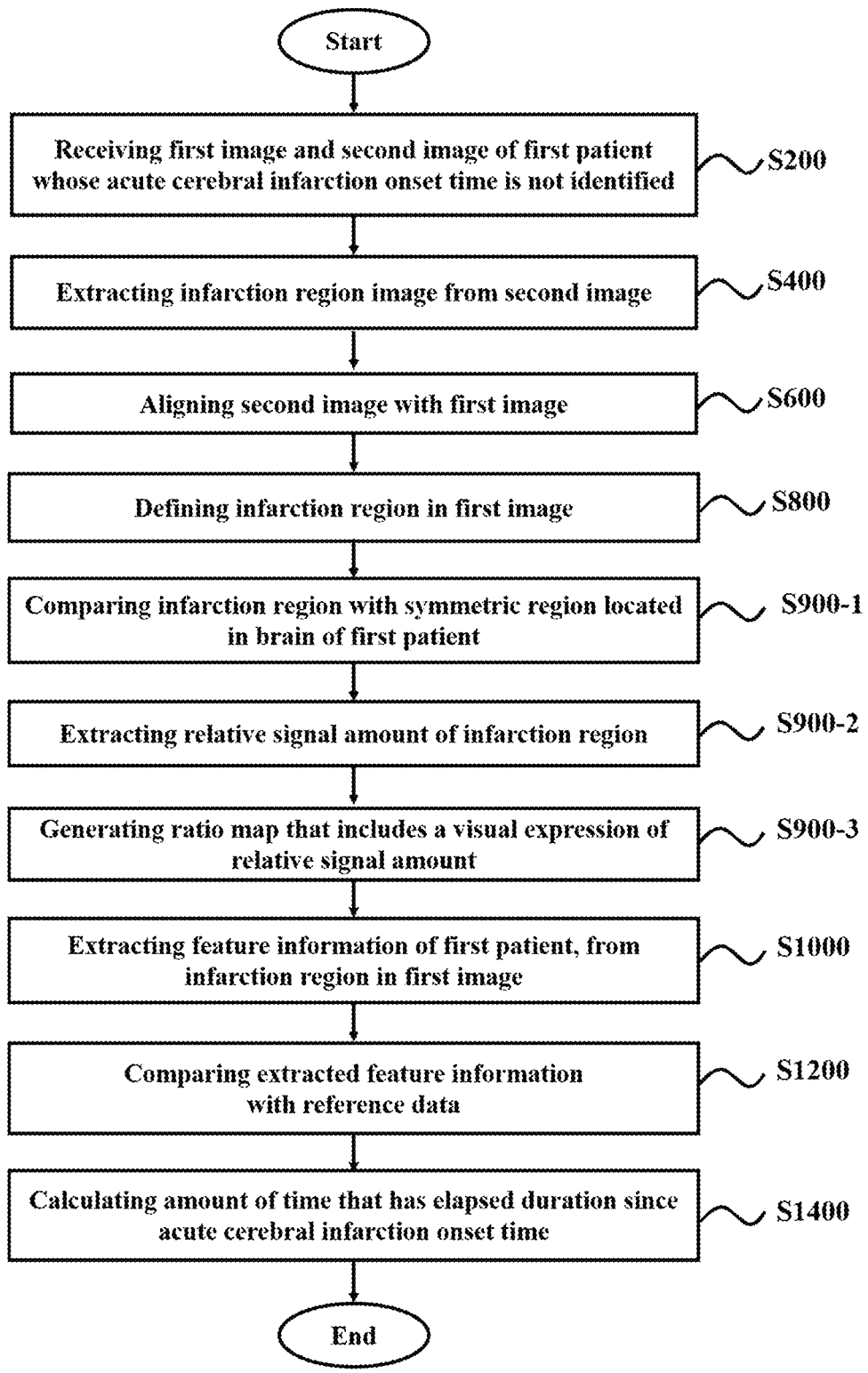
FIG. 7 is a flowchart of the acute cerebral infarction onset time estimation method that further includes a ratio map generation operation for the first image, according to some embodiments of the present disclosure.

Further, as shown in FIG. 7, in some embodiments of the present disclosure, the method further includes a step S900-3 of generating a ratio map 30 that includes a visual expression of a relative signal amount between the symmetric region and the infarction region.

Further, in some embodiments, when the processor generates the ratio map 30 based on the first image 10, the feature information includes first feature information extracted from the infarction region in the first image 10; and second feature information extracted from an infarction region in the ratio map 30 for the first image 10. That is, the processor uses at least one feature element extracted from the first image 10 itself and from the ratio map 30 for the first image 10 as feature information.

Figure 8:
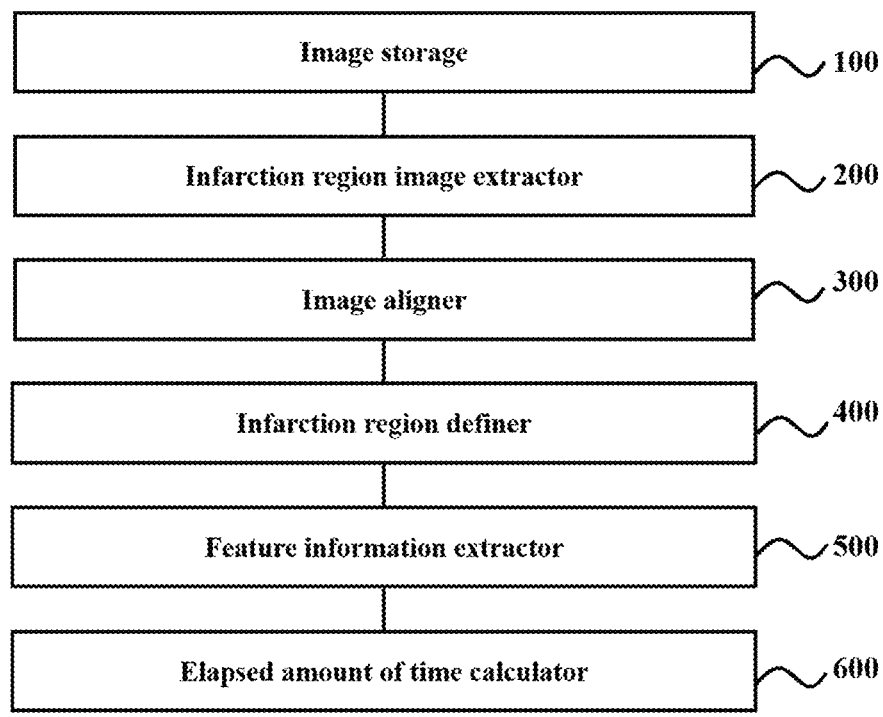
FIG. 8 is a schematic view illustrating a configuration of an acute cerebral infarction onset time estimation system, according to some embodiments of the present disclosure.

FIG. 8 is a schematic view illustrating a configuration of an acute cerebral infarction onset time estimation system, according to some embodiments of the present disclosure.

The acute cerebral infarction onset time estimation system in accordance with some embodiments of the present disclosure comprises at least one processor for estimating or calculating the acute cerebral infarction onset time. Referring to FIG. 8, the acute cerebral infarction onset time estimation system in accordance with some embodiments of the present disclosure comprises an image storage 100; an infarction region image extractor 200; an image aligner 300; an infarction region definer 400; a feature information extractor 500; and an elapsed amount of time calculator 600.

The image storage 100 stores the first image 10 and second image 20 for a first patient whose acute cerebral infarction onset time is not identified. That is, the image storage 100 receives the first image 10 and the second image 20 of the first patient from the MR image capture device, and stores the received first image 10 and second image 20.

In some embodiments, the image storage 100 is embodied as a memory present in the processor or in the processor. The memory includes at least one storage media such as a flash memory type, a hard disk type, a multimedia card micro type, a card type memory (for example, SD or XD memory), a random access memory (RAM), SRAM (static random access memory), read-only memory (ROM), EEPROM (electrically erasable programmable read-only memory), PROM (programmable read-only memory), magnetic memory, magnetic disk, or optical disk.

The infarction region image extractor 200 extracts the infarction region image from the second image 20. That is, the infarction region image extractor 200 extracts the infarction region image by grasping the boundary of the infarction region in the second image 20 (i.e., DWI image).

The image aligner 300 aligns the second image 20 with the first image 10. In some embodiments, the image aligner 300 performs the alignment based on a skeleton or brain shape in the first image 10 and second image 20.

The infarction region definer 400 defines the infarction region in the first image 10, based on a result of the alignment of the second image 20 with the first image 10. That is, the infarction region definer 400 superimposes a boundary of the infarction region within the diffusion-weighted image (i.e., DWI image) in which the infarction region of the acute cerebral infarction patient appears within a short period of time since the onset time on the fluid-attenuated inversion recovery image (i.e., FLAIR image), thereby to define an infarction region in the FLAIR image.

The feature information extractor 500 extracts feature information of the first patient, from the infarction region of the first image 10. The feature information includes at least one feature element extracted from the specific region of the image data, that is, the MR image. In some embodiments, the feature information extractor 500 applies at least one of Gray Level Cooccurrence Matrix (GLCM), Run-Length Matrix (especially, Gray Level Run-Length Matrix (GLRLM)), and Local Binary Pattern (LBP), to the signal intensity and gradient of the infarction region, to extract the feature information.

The elapsed amount of time calculator 600 compares the extracted feature information with the reference data, and calculates the elapsed amount of time since the acute cerebral infarction onset time, based on a result of the comparison of the extracted feature information with reference data. That is, the elapsed amount of time calculator 600 calculates the elapsed amount of time since the onset of the acute cerebral infarction of the first patient based on the feature information in the infarction region of the second image 20 (i.e., DWI image) within the first image 10 (i.e., FLAIR image).

Each of the infarction region image extractor 200, image aligner 300, infarction region definer 400, feature information extractor 500, and elapsed amount of time calculator 600 is contained in a particular processor or a particular computer, in software or hardware manner.

Figure 9:
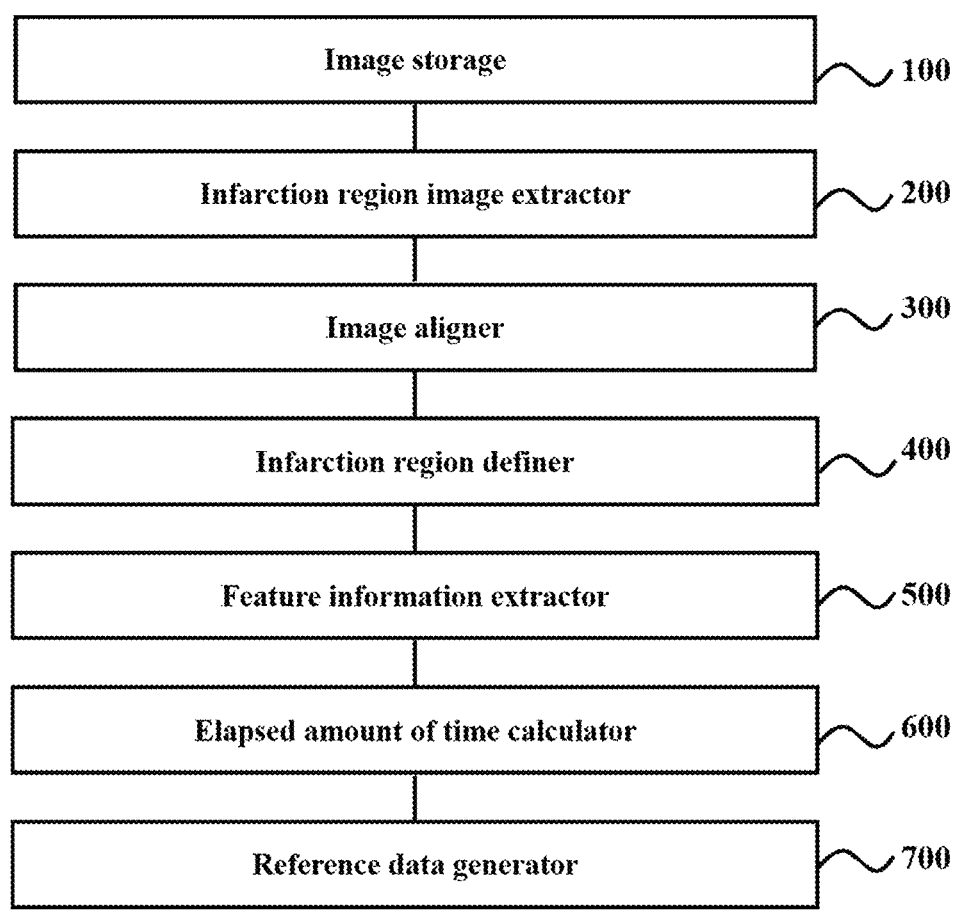
FIG. 9 is a schematic view illustrating a configuration of an acute cerebral infarction onset time estimation system, according to some embodiments of the present disclosure.

Further, as shown in FIG. 9, an acute cerebral infarction onset time estimation system according to some other embodiments of the present disclosure further comprises a reference data generator 700. The reference data generator 700 generates the reference data as the support vector machine, based on the first image 10 and the second image 20 of each of a plurality of second patients. In some embodiments, the reference data generator 700 performs following operations: classifying the plurality of second patients into a training group, a validating group, and a testing group; extracting feature information of each of second patients classified into the training group, from a first image 10 of the each of the second patient classified into the training group, by performing an alignment of the first image of the each of the second patients classified into the training group with a second image of the each of the second patients classified into the training group; training the support vector machine by using the feature information of the second patients classified into the training group; determining a type of the support vector machine by using the validating group; and applying the testing group to the determined support vector machine type to determine whether the determined support vector machine type is to be defined as the reference data.

Figure 10:
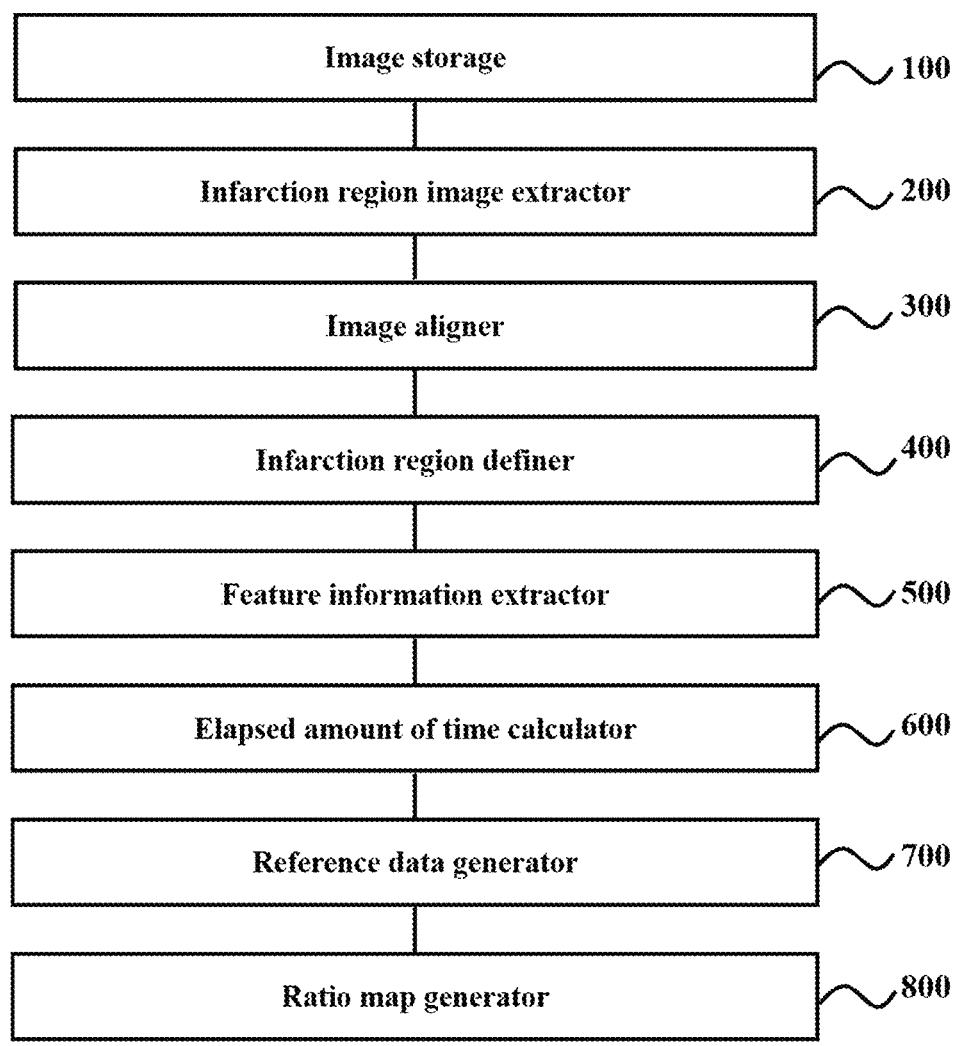
FIG. 10 shows a schematic view illustrating a configuration of an acute cerebral infarction onset time estimation system, according to some embodiments of the present disclosure.

Further, as shown in FIG. 10, an acute cerebral infarction onset time estimation system according to some other embodiments of the present disclosure further includes a ratio map generator 800. The ratio map generator 800 is configured to compare the infarction region with a symmetric region located in a brain of the first patient and being symmetrical to the infarction region, extract a relative signal amount of the infarction region, based on a result of the comparison of the infarction region with the symmetric region; and generate the ratio map 30 that includes a visual expression of a relative signal amount between the symmetric region and the infarction region. Since the MR image is represented using a relative signal amount within an image to be captured, the signal amount of the infarction region does not employ an absolute signal amount. Therefore, using characteristics of the brain that the brain is symmetrically configured based on a specific boundary line, the ratio map generator 800 compares the infarction region with a symmetric region located in a brain of the first patient and being symmetrical to the infarction region in the first image 10 to extract a relative signal amount of the infarction region. Therefore, as the relative signal amount of the infarction region in the first image 10 is calculated, the feature information extracted from the infarction region in the first image 10 of the first patient is compared with the feature information extracted from the infarction region of the first image 10 of the second patient. In this connection, the feature information includes: first feature information extracted from the infarction region in the first image 10; and second feature information extracted from an infarction region in the ratio map 30 for the first image 10.

In some embodiments, the acute cerebral infarction onset time estimation method according to some embodiments of the present disclosure as described above may be implemented using a program (or application) to be executed in combination with a computer as hardware, which may be stored in a non-transitory computer readable recording medium.

The above-mentioned program may include codes encoded in a computer language such as C, C++, JAVA, python, or machine language which a central processing unit (CPU) of a processor or a computer can read via a device interface of a processor or a computer. Thus, when the computer reads and executes the program, the program may perform the method. These codes may include functional codes related to functions that define necessary functions to execute the method, or may include executable procedure-related control codes necessary for the processor of the computer to execute the functions in accordance with a predetermined procedure. Further, these codes may further include memory reference-related code that indicates where additional information or media needed for the execution of the functions by the computer's processor is addressed to any location (address) in the computer's internal or external memory. Further, when the computer's processor needs to communicate with any other computer or server at a remote location to execute the functions, the codes may further include communication related codes indicating, for example, how to communicate with any other computer or server remotely using a communication module of the computer, and what information or media as transmitted or received therebetween during communication.

The storage medium is not a medium for storing data for a short time such as a register, a cache, a memory, etc., but means a medium that semi-permanently stores data and is capable of being read by a device. Specifically, examples of the storage medium include, but are not limited to, ROM, RAM, CD-ROM, magnetic tape, floppy disk, optical data storage, and the like. That is, the program may be stored on various recording media on various servers that the computer can access, or on various recording media on the user's computer. Further, the medium may store therein computer readable codes as distributed over a networked computer system and as read by the computer in a distributed manner.

According to the embodiments of the present disclosure as described above, the acute cerebral infarction onset time can be estimated from a patient whose acute cerebral infarction onset time is not identified. This may reduce the number of patients who miss the timing of thrombolysis due to the inability to determine whether the acute cerebral infarction is capable of being cured using thrombolysis.

Further, because the computer quickly performs the elapsed duration calculation of the acute cerebral infarction automatically based on the fluid-attenuated inversion recovery image (i.e., FLAIR image) and the diffusion-weighted image (i.e., DWI image), the medical staff may figure out the elapsed duration after the patient's acute cerebral infarction starts, and may determine immediately whether to start the thrombolysis for the patient. Therefore, a time required for the medical staff to determine whether or not the thrombolysis is performed using the MR image reading may be reduced. This can increase the percentage of patients whose acute cerebral infarction can be treated.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for estimating an onset time of acute cerebral infarction, the method comprising:
   receiving, by a processor, from an external device, a first image and a second image of a first patient whose acute cerebral infarction onset time is not identified, the first image is a fluid-attenuated inversion recovery image, and the second image is a diffusion-weighted image;
   extracting, by the processor, an infarction region image from the second image;
   aligning, by the processor, the second image with the first image;
   defining, by the processor, an infarction region in the first image, based on a result of the alignment of the second image with the first image;
   extracting, by the processor, feature information of the first patient, from the infarction region in the first image;
   comparing, by the processor, the extracted feature information with reference data;
   calculating, by the processor, an amount of time that has elapsed since the acute cerebral infarction onset time, based on a result of the comparison of the extracted feature information with the reference data;
   comparing, by the processor, the infarction region with a symmetric region located in a brain of the first patient and being symmetrical to the infarction region;
   extracting, by the processor, a relative signal amount of the infarction region, based on a result of the comparison of the infarction region with the symmetric region; and
   generating, by the processor, a third image that shows a ratio map of a pixel comparison of pixels of the symmetric region with corresponding pixels of the infarction region,
   wherein the feature information includes:
      first feature information extracted from the infarction region in the first image; and
      second feature information extracted from an infarction region in the third image.

2. The method of claim 1, wherein the reference data includes:
   feature information of at least one second patient, contained in an infarction region of a first image of the at least one second patient, the second patient is a patient whose acute cerebral infarction onset time is identified; and
   information on an amount of time that has elapsed since an acute cerebral infarction onset time of the at least one second patient.

3. The method of claim 2, further comprising:
   generating, by the processor, the reference data as a support vector machine, based on first and second images of a plurality of second patients,
   wherein the generating of the reference data comprises:
      classifying the plurality of second patients into a training group, a validating group, and a testing group;
      extracting feature information of each of second patients classified into the training group, from a first image of the each of the second patients classified into the training group, by performing an alignment of the first image of the each of the second patients classified into the training group with a second image of the each of the second patients classified into the training group;
      training the support vector machine by using the feature information of the second patients classified into the training group;
      determining a type of the support vector machine by using the validating group; and
      applying the testing group to the determined support vector machine type to determine whether the type of the support vector machine is to be defined as the reference data.

4. The method of claim 2, wherein the reference data is classified into detailed groups according to gender or age information of second patients, and
   wherein the calculating of the elapsed amount of time comprises defining detailed groups to be compared with the feature information of the first patient, based on age information or gender information of the first patient.

5. The method of claim 1, wherein the extracting of the infarction region image from the second image comprises:
   normalizing an intensity of an apparent diffusion coefficient map of the second image; and
   extracting the infarction region image via an absolute reference value search in the normalized apparent diffusion coefficient map.

6. The method of claim 1, further comprising:
   determining, by the processor, whether the elapsed amount of time is within a reference duration; and
   outputting, by the processor, a signal for notifying the determination result.

7. The method of claim 1, wherein the aligning of the second image with the first image comprises
   aligning of the second image with the first image by applying at least one of an enlargement, a shrinkage, a symmetrical movement, and a rotation, to the first image or the second image, based on a skeleton position in the first image or the second image.

8. The method of claim 1, wherein the extracting of the feature information comprises
   extracting the feature information by applying at least one of a gray level co-occurrence matrix, a run-length matrix and a local binary pattern, to signal intensity and gradient of the infarction region.

9. A non-transitory computer readable recording medium storing a computer program coupled to a computer device including a processor to execute the method for estimating an onset time of acute cerebral infarction, according to claim 1.

10. A system for estimation of an acute cerebral infarction onset time, the system comprising:
   an image storage that stores a first image and a second image of a first patient whose acute cerebral infarction onset time is not identified, the first image is a fluid-attenuated inversion recovery image, and the second image is a diffusion-weighted image;
   an infarction region image extractor that extracts an infarction region image from the second image;
   an image aligner that aligns the second image with the first image;
   an infarction region definer that defines an infarction region in the first image, based on a result of the alignment of the second image with the first image;
   a feature information extractor that extracts feature information of the first patient, from the infarction region of the first image;

an elapsed amount of time calculator that compares the extracted feature information with reference data, and calculates an amount of time that has elapsed since the acute cerebral infarction onset time, based on a result of the comparison of the extracted feature information with reference data; and a ratio map generator configured to:
  compare the infarction region with a symmetric region located in a brain of the first patient and being symmetrical to the infarction region;
  extract a relative signal amount of the infarction region, based on a result of the comparison of the infarction region with the symmetric region; and
  generate a third image that shows a ratio map of a pixel comparison of pixels of the symmetric region with corresponding pixels of the infarction region,
wherein the feature information includes:
  first feature information extracted from the infarction region in the first image; and
  second feature information extracted from an infarction region in third image.

11. The system of claim 10, wherein the reference data includes:
  feature information of at least one second patient, contained in an infarction region of a first image of the at least one second patient, the second patient is a patient whose acute cerebral infarction onset time is identified; and
  information on an amount of time that has elapsed since an acute cerebral infarction onset time of the at least one second patient.

12. The system of claim 10, further comprising:
a reference data generator that generates the reference data as a support vector machine, based on first and second images of a plurality of second patients,
wherein the reference data generator is configured to:
  classify the plurality of second patients into a training group, a validating group, and a testing group;
  extracts feature information of each of second patients classified into the training group, from a first image of the each of the second patients classified into the training group, by performing an alignment of the first image of the each of the second patients classified into the training group with a second image of the each of the second patients classified into the training group;
  train the support vector machine by using the feature information of the second patients classified into the training group;
  determine a type of the support vector machine by using the validating group; and
  apply the testing group to the determined support vector machine type to determine whether the determined support vector machine type is to be defined as the reference data.

* * * * *